United States Patent [19]

Laurenson, Jr.

[11] Patent Number: 5,175,106

[45] Date of Patent: * Dec. 29, 1992

[54] METHOD AND APPARATUS FOR IMPROVING EFFICIENCY OF FLUID USE AND ODOR CONTROL IN IN-VESSEL COMPOSTING SYSTEMS

[76] Inventor: John G. Laurenson, Jr., 3223 Harbor Drive, Camache Island Villas, St. Augustine, Fla., 32084

[*] Notice: The portion of the term of this patent subsequent to Jun. 6, 2006 has been disclaimed.

[21] Appl. No.: 484,392

[22] Filed: Feb. 23, 1990

Related U.S. Application Data

[60] Continuation-in-part of Ser. No. 268,593, Nov. 7, 1988, which is a division of Ser. No. 643,080, Aug. 22, 1984, Pat. No. 4,837,153.

[51] Int. Cl.⁵ .................. C12N 1/00; C12M 1/04; C12M 1/12
[52] U.S. Cl. .................. 435/243; 435/266; 435/311; 435/313; 435/818; 435/819; 422/184; 71/9
[58] Field of Search .................. 422/5, 184; 435/243, 435/309, 313, 818, 311, 819, 266, 287, 316, 315; 210/346, 347, 457, 620, 221.2; 71/9; 261/122, 65; 137/829, 832; 34/15, 165, 22, 26, 29, 32, 34, 57 R, 57 B; 55/74, 96, 98, 267, 387, 418, 419, 467, 468, 476

[56] References Cited

U.S. PATENT DOCUMENTS

| | | |
|---|---|---|
| 3,114,622 | 12/1963 | Hardy . |
| 3,357,812 | 12/1967 | Snell . |
| 4,203,755 | 5/1980 | Ruckstuhl . |
| 4,256,710 | 3/1981 | Azuma et al. ............ 423/210 |
| 4,267,039 | 5/1981 | Ryan ..................... 210/767 |
| 4,374,804 | 2/1983 | Easter .................... 435/819 |
| 4,410,349 | 10/1983 | Laurenson, Jr. ............ 71/9 |
| 4,436,817 | 3/1984 | Nemetz ................... 435/313 |
| 4,482,633 | 11/1984 | Roediger ................. 435/311 |
| 4,550,010 | 10/1985 | Chelu .................... 422/4 |
| 4,798,801 | 1/1989 | Hitzman .................. 435/313 |
| 4,837,153 | 6/1989 | Laurenson, Jr. ........... 435/243 |
| 4,956,002 | 9/1990 | Egarian .................. 422/184 |

Primary Examiner—Robert J. Warden
Assistant Examiner—William H. Beisner
Attorney, Agent, or Firm—Foley & Lardner

[57] ABSTRACT

A method for improving the efficient use of fluid and for improving the odor control in in-vessel composting. The method includes the re-use of exhaust fluid from a first composting reactor in a second composting reactor in a single multiple chain system. Improved odor control is achieved by the provision of an odor control device interposed in the fluid stream from the first composting reactor to the second composting reactor and passing exhaust fluid from the first reactor through the odor control device to remove pollutants therefrom before re-use in the second composting reactor. The exhaust fluid from the second composting reactor may also be passed through the odor control device before it is exhausted to the atmosphere.

19 Claims, 6 Drawing Sheets

D = DRAINS TO WASTEWATER TREATMENT FACILITY

D=DRAINS TO WASTEWATER TREATMENT FACILITY

METHOD AND APPARATUS FOR IMPROVING EFFICIENCY OF FLUID USE AND ODOR CONTROL IN IN-VESSEL COMPOSTING SYSTEMS

This application is a continuation-in-part of application Ser. No. 268,593, filed Nov. 7, 1988, which is a division of application Ser. No. 643,080, filed Aug. 22, 1984, now U.S. Pat. No. 4,837,153.

BACKGROUND OF THE INVENTION

The present invention relates to in-vessel composting. More particularly, the invention relates to a new and improved method and apparatus for in-vessel composting for improved fluid use efficiency and pollution control.

It has long been recognized that vast quantities of organic waste materials are being produced annually. As the world's population increases so does its capacity to produce waste materials. The disposal of these waste materials represent difficult disposal problems. Their disposal takes up valuable land, and monopolizes large amounts of time, energy, effort and capital to overcome the burden of the ever increasing quantities of organic waste material.

Composting provides an important part of the solution to reduce the problems associated with organic waste material disposal. Further, composting can provide materials that serve as important basic building block materials for such industries as the construction industry and the agriculture industry.

Composting for the most part is a time consuming, energy intensive, non-uniform process. Various composting apparatus and methods are shown in U.S. Pat. Nos. 3,114,622; 3,357,812; and 4,203,755.

U.S. Pat. No. 3,114,622, issued Dec. 17, 1963 to W. Hardy, discloses an apparatus utilized as a waste material converter. The converter includes a plurality of screw augers having holes therein for the introduction of air into the waste pile. U.S. Pat. No. 3,357,812, issued Dec. 12, 1967 to J.R. Snell, discloses an apparatus for composting organic waste material utilizing a fixed pipe system located beneath the composting pile for accomplishing reversible air flow. U.S. Pat. No. 4,203,755, issued May 20, 1980 to K. Ruckstuhl, discloses an apparatus for treating waste material wherein a plurality of pipes are disposed within the composting mass for the discharge of gaseous products of decomposition.

One of Applicant's previous inventions provides a device that equalizes air distribution throughout the compost pile as set forth in U.S. Pat. No. 4,410,349, issued Jul. 8, 1983 to Applicant. This equalization reduces air pressure thereby reducing horsepower, and the associated energy needed to generate the required air distribution. The air distribution equalization enhances process controls and removes or inserts moisture in the system, as desired to improve composting efficiency. Further, the device reduces the overall length of the process air path to prevent compost pile hot spots and dead spots to provide a more uniform composting process. That invention provides improved fluid flow control for the air distribution lances utilized in compost piles.

Another of Applicant's previous inventions, as set forth in grand parent U.S. application Ser. No. 643,080, incorporated herein by reference, filed Aug. 22, 1984, now U.S. Pat. No. 4,837,153, provides an improved fluid flow control method for composting organic waste material. The improved fluid flow control is provided by a lance having at least two separate fluid flow zones to provide a fluid flow profile in the compost. The flow zones are provided by an outer porous wall tube with a control insert tube therein, having a plurality of openings along the length thereof and spaced from the wall by gaskets to form the separate flow zones. The control insert tube can also include an internal tube valve therein, which allows for adjustment of the fluid flow through the insert openings.

A plurality of the lances disclosed in U.S. Pat. No. 4,837,153 are preferably used in the composting system. The lances are coupled to a manifold system for the injection and evacuation of fluid or air flow in distinct substantially uniform injection and evacuation patterns substantially equally spaced from one another. The manifold defines the injection and evacuation patterns in a substantially vertical plane, while the lances define the patterns in a horizontal plane.

In yet another of Applicant's inventions, described in copending application Ser. No. 190,340, filed May 5, 1988, there is provided a new and improved biofiltration air control distribution method and system for use in earth filters or biotowers. The biofiltration apparatus described in that application uses the lances described in U.S. Pat. No. 4,837,153, the disclosure of which is incorporated herein by reference, preferably coupled to a manifold system for the injection and evacuation of fluid or air flow in the biofiltration apparatus.

While the improved fluid flow control methods and apparatus disclosed in Applicant's prior applications and patents have provided marked improvements to in-vessel composting systems, in recent times of stricter environmental regulations it has become even more desirable to minimize stack discharges and emissions during the operation of a compost facility. This is especially true in urban areas where any discharge of malodorous compounds is unacceptable. The new in-vessel composting system described and claimed herein not only reduces the quantity of fluid discharged into the atmosphere from the composting process, but also removes particulates and noxious and odorous gases from the exhaust fluid before it is discharged.

SUMMARY OF THE INVENTION

The present invention provides a new and improved in-vessel composting method and system for the composting of organic waste material and an improved odor control device adapted to be used integrally with the in-vessel composting system for the removal of particulates and noxious and odorous compounds from the exhaust fluid before it is exhausted from the compost system.

The improved in-vessel composting system of the present invention is predicated on the recycling and re-use in a second downstream composting reactor of process fluid (typically air) which has already been used for aeration of the composting mass in an upstream composting reactor. A further improvement to the in-vessel composting system lies in treating the process fluid exhausted from the first, upstream composting reactor (i.e. bioreactor) prior to recycling the process fluid for re-use in the second, downstream composting reactor (i.e. cure reactor) in the odor control device. The odor control device may form an integral part of the composting system and may also be used to treat exhaust fluid from the second, downstream composting reactor as well as from the first, upstream composting reactor.

The re-use of fluid which has already been used in the upstream composting reactor, i.e., bioreactor, provides the composting process of the present invention with several advantages. Because the re-used fluid is at ambient temperature and, preferably, saturated with water vapor, its use assists in controlling the temperature in the downstream composting reactor, i.e., cure reactor, and also assists in maintaining a slow drying of the aging compost therein. Re-use of the air also allows higher fluid flow rates, particularly where the fluid is air, in the cure reactor owing to its slightly lower oxygen content. Because there is less oxygen available to the microbes from the re-used fluid (and thus the atmosphere supplied to the microbes) cure reactor temperatures can be maintained at a lower level during curing. An additional benefit is that the higher fluid flow rates also contribute to an improved fluid flow pattern over the length of the lances described in my U.S. Pat. No. 4,837,153 when such lances are used in this new composting system. The higher fluid flow rate enhances drying and the lower curing temperature limits the destruction of the compost's fertilizing value thereby providing a higher quality fertilizer product from the composting system.

The re-use of the bioreactor exhaust fluid as the process fluid for the cure reactor reduces stack discharge from the composting system. The bioreactor exhaust fluid may be cleansed of malodorous gases when used at least in part as the processing fluid for the cure reactor. Further, in such a cycle, the cure reactor acts as a biofilter to remove malodorous gases that have not been removed in the odor control system. Re-use of the bioreactor exhaust fluid is particularly advantageous in the compost system of the present invention because the biofiltration medium, that is, the curing compost, is continually replenished through the daily addition of curing compost and removal of cured compost from the curing reactor. Oversaturation of the bio-filter media with adsorbed compounds and moisture is thereby avoided.

The inclusion of the odor control device integral to the process provides a further advantage to the overall process in that particulates, and noxious and malodorous gases may be removed from the process before the process fluid is exhausted from the composting system. When an odor control system as described herein is installed integral to the composting system the re-used process fluid is treated both before and after re-use to remove particulates and noxious or odorous compounds.

DETAILED DESCRIPTION OF THE PREFERRED EMBODIMENTS

Figure 1:
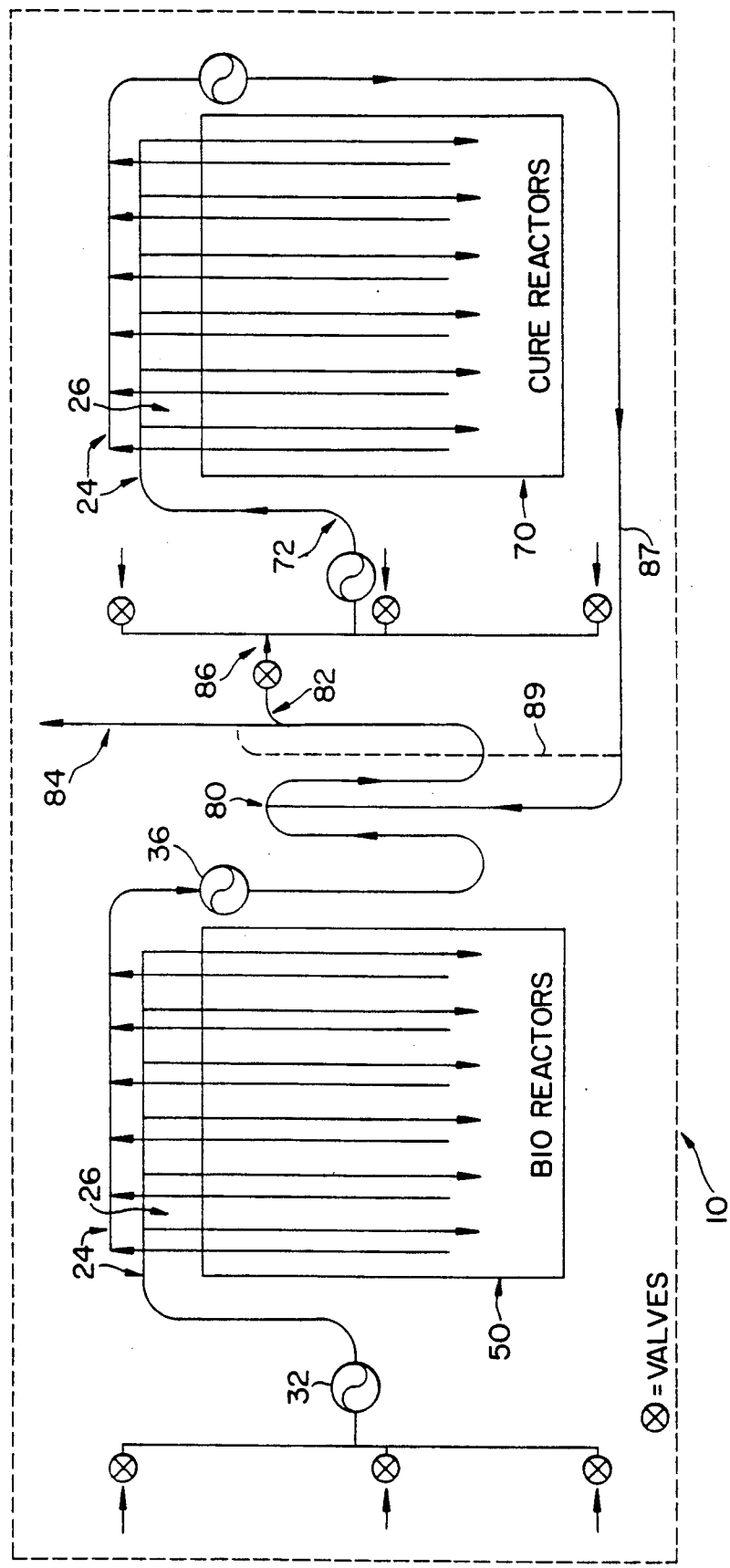
FIG. 1 is a schematic illustration of an in-vessel composting system and method of the present invention and further shows the fluid flow schematic for process, exhaust and odor control for such a single train composting system.
Figure 2:
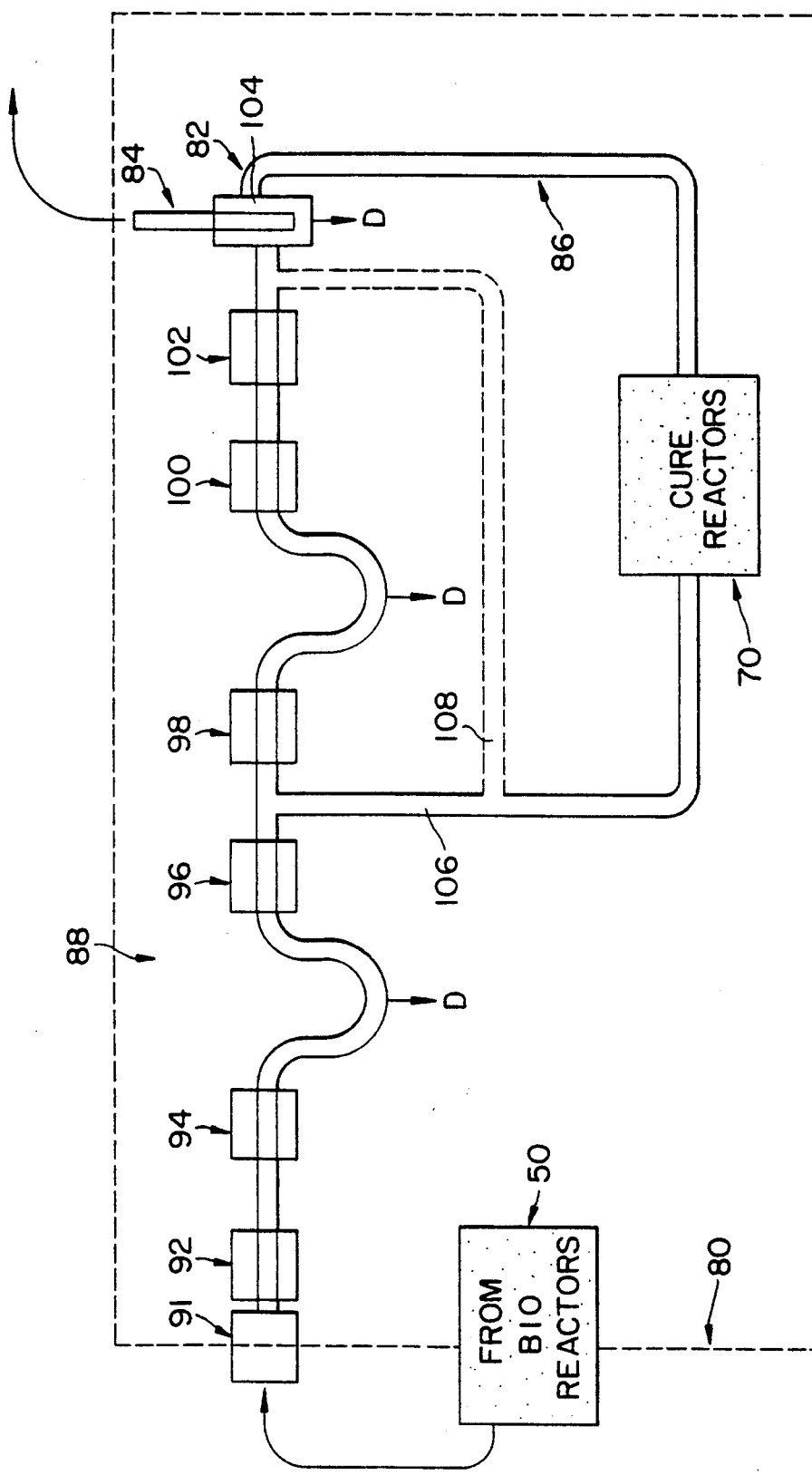
FIG. 2 is a schematic illustration of an odor control device for use in the in-vessel composting system of FIG. 1.

FIGS. 1 and 2 generally depict the composting system and odor control device of the present invention for a single train system. FIG. 1 illustrates the fluid flow schematic for process and exhaust fluid of the in-vessel composting system of the present invention including the fluid flow through an integral odor control device, while FIG. 2 illustrates one odor control device in greater detail.

Referring now to FIG. 1, there is illustrated an in-vessel composting system 10 which includes a bioreactor 50, a cure reactor 70 and an integral odor control device 80 disposed in the process stream between the bioreactor 50 and the cure reactor 70.

Figure 5:
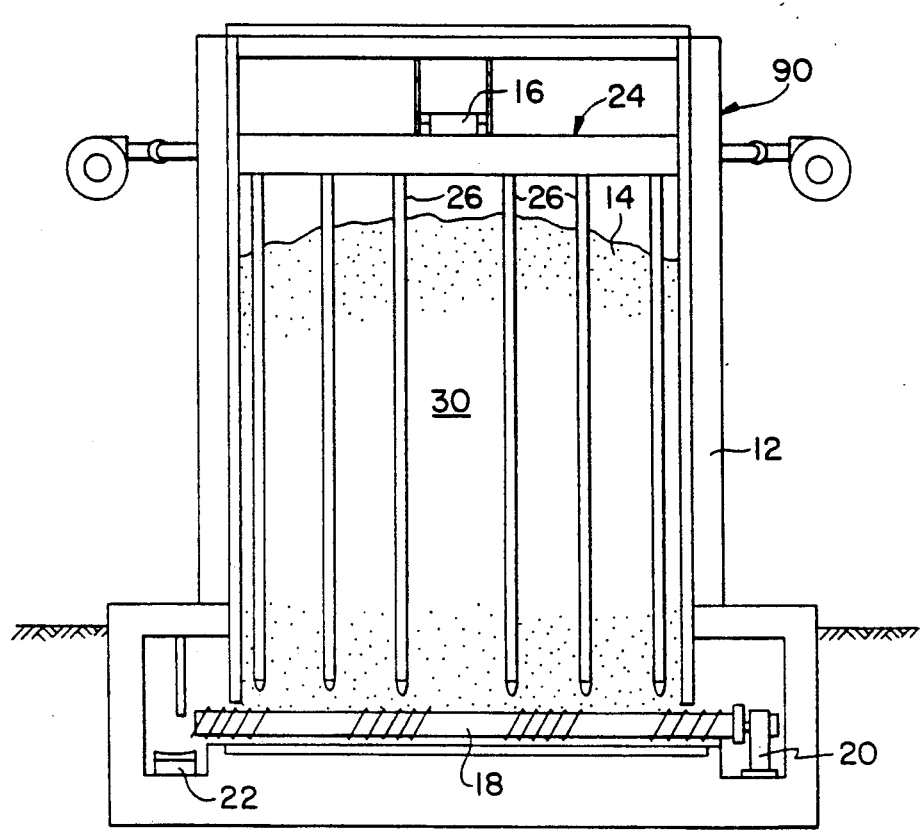
FIG. 5 is a vertical sectional view of a bioreactor and/or cure reactor suitable for use in the in-vessel composting system of the present invention.

The bioreactor 50 and the cure reactor 70 preferably comprise an air injection and evacuation system as described in greater detail in U.S. Pat. No. 4,837,153 and copending application Ser. No. 268,593, filed Nov. 7, 1988. By way of example, as shown in FIG. 5, the bio and cure reactors include a containment structure 12 housing a fluid distribution system 90. The containment structure 12 receives material 14 to be composted by an infeed conveyor and distributor 16, located near the upper portion of the structure 12. Once composted the finished product is discharged near the bottom portion of the containment structure 12 by a discharge screw 18 driven by a suitable drive system (not shown). The finished product is discharged onto a discharge conveyor 22 adapted to carry the material to loading and handling facilities for further processing or shipping.

The containment structure 12 as depicted in FIG. 5 is basically rectangular in configuration; however the fluid distribution system 90 incorporates adaptability and flexibility so as to be utilized in containment structures of various sizes and shapes, such as circular structures and A-Frame structures, for example.

Figure 7:
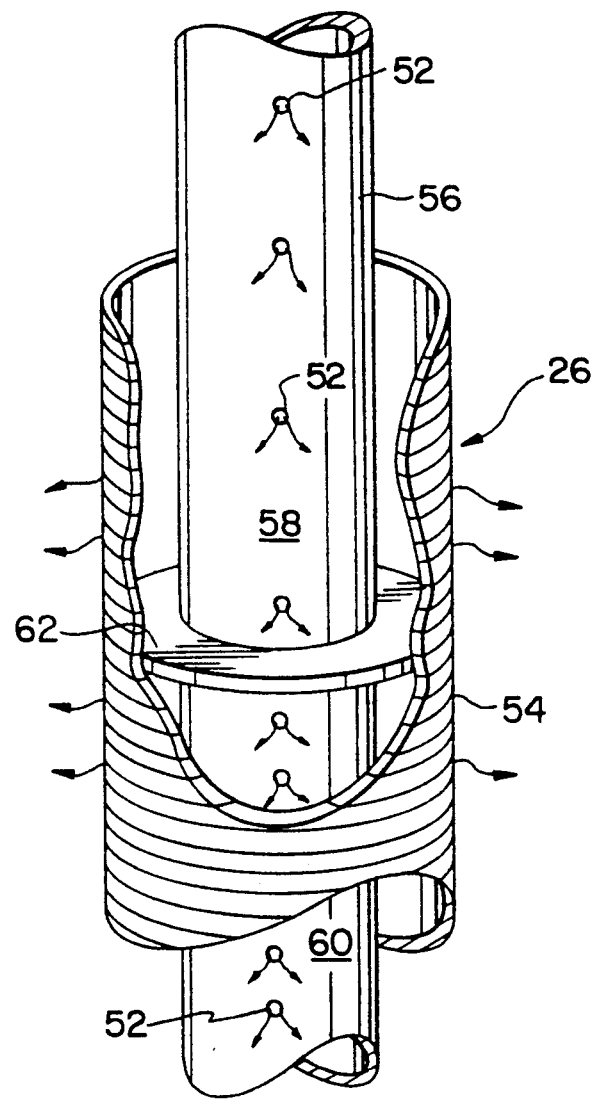
FIG. 7 is a partial fragmentary elevational view of an embodiment of the lances that may be used in the bioreactor and cure reactor of the present invention.

The fluid or air distribution system 90 includes a manifold 24 for directing fluid flow towards and away from a plurality of lances 26 (FIG. 7). The manifold 24 is situated near the upper end portion of the containment structure 12 and is suspended in a substantially horizontal plane. The lances 26 are coupled to the manifold 24 at various points along the length of a plurality of box beams 28 and project downward into the material 14 in a compost pile 30.

The manifold 24 is constructed so as to deliver fluid flow to the lances 26 by one or more fluid handlers or blowers 32 through one or a plurality of manual or automatic valves 34. The fluid flow can be reversed to remove fluid from the lances 26 and hence the compost pile 30 by a second set of exhaust blowers 36 and valves 38. Preferably, a substantially uniform pattern of fluid injection into and a substantially uniform pattern of fluid evacuation from the compost pile 30 through the lances 26 is created which provides the advantages described in U.S. Pat. No. 4,837,153. Preferably, the lances described in U.S. Pat. No. 4,837,153 and copending application Ser. No. 268,593 are used in the bioreactor 50 and the cure reactor 70. Referring to FIG. 7, each lance 26 includes an outer fluid flow wall or tube 54. The tube 54 forms the body of the lance 26 and preferably can be formed from a stainless steel mesh or screen such as sold under the trade name Wedgewire. The grid size can be chosen for the particular compost application, and typically can be on the order of 0.02 inches.

The lance 26 includes a fluid flow characterizing control insert 56. The insert 56 includes the plurality of apertures or openings 52 spaced along the length thereof. The apertures 52 are typically on the order of 0.03 to 0.0625 inches in diameter, which insures that they will not be blocked by particles which can pass through the outer wall 54. The apertures 52 typically have a spacing which varies along sections of the insert 56 to provide the desired fluid flow profile into the compost.

The apertures 52 are illustrated with a first spacing along the length of an insert section 58 and a second spacing along the length of a second insert section 60.

The fluid (e.g., air) flow control profile is provided by the outer wall 54, the insert 56, the apertures 52 along with a plurality of fluid control gaskets or dams 62 (only one of which is illustrated). The gaskets 62 are mounted on the insert 56 and spaced to provide a seal between separate fluid flow zones, such as the sections 58 and 60, which prevents internal short circuiting of the desired fluid flow profile from high to low pressure zones. The gaskets 62 preferably can be made of viton rubber. The insert 56 with the gaskets 62 can just be inserted into and removed from the tube 54 without removal of the tube 54, through the sealable opening 48 in the top of the manifold 24. The insert 56 and gaskets 62 then easily can be removed to adjust for fluid flow changes as needed.

Figure 6:
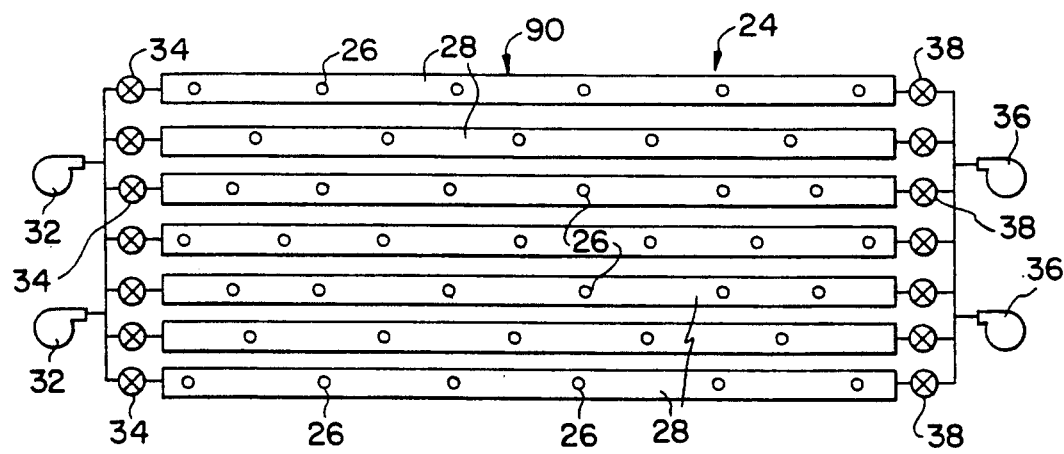
FIG. 6 is a top schematic view of the system of FIG. 5.

As shown in FIG. 6, the fluid handlers 32 and 36 and the valves 34 and 38 are adapted to either manually or automatically, attendant to sensed process condition or programmed timing sequence, reverse the fluid flow in the manifold 24. The fluid flow reversal changes the fluid flow within the compost pile 30, but still maintains substantially uniform patterns of fluid injection and fluid evacuation. This fluid flow reversal further allows greater control over the composting operation to reduce composting time and obtain a more uniform end product.

Lance length, lance spacing, as well as the pattern and size of orifices in the lance are dictated by the compost characteristics, and fluid (e.g., air) flow requirements. Further the size and shape of the containment structure 12 dictates the size of the lances. For example in an A-Frame containment structure manifolds or beams will be placed at various levels to accommodate the sloping sides to maintain uniform patterns of fluid flow out to the edges of the structure. This will also necessitate different lengths of lances which can be formed in interconnecting segments.

The fluid injection and distribution system 90 provides substantially uniform patterns of fluid injection and evacuation in the compost pile. These patterns reduce the process fluid path which reduces fluid pressure, and reduces horsepower which in turn lessens energy consumption. The reversing of the fluid flow in the fluid distribution system provides greater controlling of process conditions to provide a more uniform compost pile by negating the cooling effect of fluid injection in one area which tends to produce dead spots, i.e., non-composting areas.

In accordance with the invention, referring again to FIG. 1, heated fresh process fluid (e.g., air) is introduced into the bioreactor 50 by a first set of injection blowers 32 and through the lances 26 of the fluid injection and evacuation device. Reversal of the fluid flow in the manifold 24 by a second set of exhaust blowers 36 and valves 38 removes process fluid from the reactor. The bioreactor exhaust fluid, which contains about 19% oxygen when the fresh process fluid is air, is, in the preferred embodiment, passed through the odor control device 80 for pollution control, including the removal of particulates and noxious and malodorous gases and contaminants. The treated fluid, when the fresh process fluid is air, that exits the odor control device 80 contains about 17% oxygen at 25 to 45° C. Preferably the fluid is treated in the odor control device 80 so as to be saturated with water vapor in order to assist in controlling the temperature in the cure reactor 70 and to assist in maintaining a slow drying of the aging compost in the cure reactor 70.

The treated effluent fluid from the odor control device 80 is passed to a discharge stack area 82 where it is split into two streams 84, 86. The stream 84 is exhausted from the in-vessel composting system 10. The stream 86 is passed to the inlet 72 of the cure reactor 70 where it is re-used by the cure reactor as process fluid. The re-used treated fluid may be introduced into the cure reactor 70 through the lances 26 of the fluid injection and distribution device of the type described above and becomes the cure reactor process fluid. Cure reactor process fluid is removed from the cure reactor 70 by an exhaust manifold system of the type described above which reverses the flow of fluid through the lances 26. The cure reactor exhaust fluid contains about 15% oxygen when the process fluid is air and is returned to the odor control device 80 via a line 84 for further treatment or is released to the exhaust stream 84 via a line 89. The exhaust fluid from the cure reactor 70 has been biofiltered by the cure reactor 70 and depending upon the type of sludge, this may be sufficient odor control.

The re-use of process fluid from the bioreactor 50 by the cure reactor 70 as described provides a more efficient use of the process fluid by reducing the total plant fluid flow through the composting system 10. In some cases fluid flow may be reduced by up to 50% as compared to current designs. The re-use of process fluid also eliminates the need for dilution fluid from an outside source before exhausting the fluid to the atmosphere to dilute the pollutant concentration, it reduces the total quantity of fluid treated, it reduces the total quantity of exhaust fluid from the system and it improves the odor emissions of the system.

In accordance with another aspect of the invention the odor control device 80 includes at least one, and optionally, a plurality of zones for the treatment of exhaust fluid from the bioreactor 50 and/or the cure reactor 70. The odor control device 80 works in conjunction with the fluid injection and distribution system in the overall composting system 10. The fluid injection and distribution system successfully collects the exhaust fluid from either or both the bioreactor 50 and the cure reactor 70 and passes it to the odor control device 80 where the exhaust fluid is treated to remove particulates and noxious and malodorous compounds. Spent process fluid from the compost mass 14 in the respective reactors is collected directly through the injection and evacuation device in each compost reactor to maximize the overall efficiency of the system. By using the injection and evacuation device for the collection of the exhaust fluids, the exhaust fluids are never in contact with surrounding atmospheric air. Accordingly, both the contamination of atmospheric air with reactor exhaust fluid and the collection and treatment of large volumes of contaminated atmospheric air is avoided. In addition, the possibility of untreated exhaust fluid entering the atmosphere is virtually eliminated. As a result, the novel process of the present invention substantially reduces the total plant fluid flow through the compost facility.

In a preferred embodiment of the invention, the odor control device 80 is an integral part of the overall composting system, being disposed downstream of the bioreactor 50 and upstream as well as downstream of the cure reactor 70 and fed by exhaust fluid from both the bioreactor 50 and the cure reactor 70. Such an arrangement allows exhaust fluid from the bioreactor 50 to be treated before it is re-used and enters the cure reactor 70, and it allows exhaust fluid from the cure reactor 70 optionally to be treated twice for odor control before it is exhausted to the atmosphere.

The odor control device 80 that has been found to be particularly useful is a "plug-flow" design in which the fluid entering the odor control device 80 is caused to move through the entire odor control device 80 and through the individual treatment zones included in the odor control device 80 before it exits the odor control device. In a preferred embodiment, referring to FIG. 2, the odor control device 80 is formed as a long, circuitous closed fluid treatment train 88 which has treatment zones equipped with injection sites for various scrubbents, including water. The plug flow design of the odor control device 80 assures substantially complete contact of the fluid by the scrubbents over the entire length of the fluid treatment train 88. The device ensures that the contact time between the scrubbent and malodorous compounds will be sufficient to permit the necessary chemical reaction between them and it eliminates the possibility of short circuiting which would, in turn, lead to the premature release of exhaust fluid prior to effective removal of pollutants. In general, the fluid treatment train 88 is sized so that the fluid retention time within the train 88 is on the order of about 15 to 30 seconds. It will be appreciated that longer or shorter times may be used, depending on a variety of factors including, for example, the nature of the sludge being composted, the concentration of pollutants, the actual scrubbing operations employed and the number of scrubbing operations used and the like. While no one set of parameters is satisfactory for all composting processes, the re-use of exhaust fluid from the bioreactor 50 and the treatment of exhaust fluid from the bioreactor 50 and the cure reactor 70 should result in an exhaust fluid from the composting system 10 that is free from malodorous compounds when "sniffed" by an individual.

Turning now to FIG. 2 it can be seen that the fluid may be subjected to one or a plurality of treatment zones. The number of treatment zones and the nature of each zone will be dependent on the nature and concentration of pollutants to be removed from the fluid. Each treatment zone is designed, however, to removed some level of pollutant, with the end result being emission from the odor control device 80 that is sufficiently low in malodorous compounds as not to be detectable to the human sense of smell.

In the description that follows it will be assumed that the exhaust fluid charged to the odor control device 80 has a relatively high concentration of ammonia. In that case the preferred treatment procedure is as follows. Exhaust fluid flow through the odor control device 80 preferably begins with exhaust fluid from either or both of the bioreactor 50 and the cure reactor 70 being passed through a heat exchanger 91 to recapture from the fluid the heat produced during the composting process. This heat may be used to heat process fluid to be used elsewhere in the composting process. In addition, the heat exchanger 91 itself acts to removed pollutants from the fluid, for by the rapid reduction in the temperature of the fluid as it passes through the heat exchanger 91, many condensible gases condense out of the fluid.

After the exhaust fluid is passed through the heat exchanger 91, it enters the fluid treatment train 88 where it travels in a long, continuous, closed circuit to the discharge stack 82 of the odor control device 80. As indicated above, the fluid treatment train 88 is designed so that the retention time of the fluid therein is on the order of 15 to 30 seconds. As the fluid travels through the fluid treatment train 88 it is subjected to several treatment zones to effectively remove pollutants from the fluid.

In a first treatment zone 92 the fluid to be treated is subjected to a high volume of cold water, preferably, in the form of a fine mist in the nature of a fog. The use of a fine mist provides a high contacting rate with the pollutants and a relatively high cooling rate. Because of the high contacting rate, dust and other particulates entrained in the fluid are precipitated as well as other pollutants. The use of cold water lowers the temperature of the fluid so as to cause the condensation of condensible gases from the fluid and thereby eliminate such condensibles therefrom. The use of this single treatment zone 92 may substantially reduce the pollution level of the exhaust fluid, and may remove up to as much as 99% of particulates, and noxious and malodorous compounds that are to be removed in the odor control device.

After exiting the first treatment zone 92, the exhaust fluid may then be passed to a second treatment zone 94 where it is subjected to a coarse mist, in the nature of a light rain, and a medium volume of water. In this zone 94 the fog carried by the fluid clears, and some of the odorous compounds are drawn out of the exhaust fluid.

The exhaust fluid then may be passed to a third treatment zone 96 where it is subjected to a coarse mist, in the nature of a light rain and low volume, acid scrubbing to further remove undesirable odorous compounds. In this zone 96 the low volume acid reduces the pH of the exhaust fluid to a pH of about 6 in order to make the oxidizers used in a subsequent treatment zone more effective. The use of the acid scrubbing treatment is particularly useful where the fluid has a high ammonia concentration. On the other hand, this treatment may be eliminated or replaced with another treatment, even water, or other fluids if a high ammonia concentration is not encountered. Suitable acids are dilute solutions of mineral acids such as sulfuric acid and hydrochloric acid.

The exhaust fluid from the third treatment zone 96 is next subject to treatment with a coarse mist, in the nature of a light rain, with a medium volume of water in a fourth treatment zone 98 in order to dilute and/or remove acid from the exhaust fluid.

The exhaust fluid is then passed to a fifth treatment zone 100 where it is subjected to a coarse mist, low volume oxidizer scrubber to neutralize the acid and to raise the pH to about 8 to about 9. Sodium hypochlorite is one compost which may be satisfactorily employed as the oxidizer. The use of sodium hypochlorite also prevents the escape of chlorine gas.

The exhaust fluid is then passed through a sixth and final treatment zone 102 where it is subjected to a coarse mist and medium volume of water to remove the caustic and provide the purified exhaust fluid.

The exhaust fluid preferably next is passed to a centrifugal mist eliminator 104 where it is centrifuged to eliminate water droplets from the fluid. The centrifugal mist eliminator 104 includes the exhaust stack 84 to discharge the treated exhaust fluid and for water vapor dispersal. If the fluid has been sufficiently treated all or part of it either may be exhausted from exhaust stack 84, or may be fed to the cure reactor 70, via line 82 depending on the fluid flow requirement of the cure reactor. If further treatment is required or if the fluid flow requirement of the cure reactor 70 so requires, the treated exhaust fluid is fed via a line to the cure reactor 70. When the fluid is exhausted from the cure reactor 70, it then can be returned to the treatment zone 98 via a line 106 or can then be exhausted by a bypass line 108. It will be appreciated that the exhaust fluid from the odor control device 80 is relatively moist, especially compared to ambient air that could be brought in for use as the process fluid. The use of this relatively moist exhaust fluid from the odor control device 80 is advantageous because it prevents the sludge in the cure reactor from drying out too much during curing, and assist in providing a compost have improved fertilizing properties.

Figure 3:
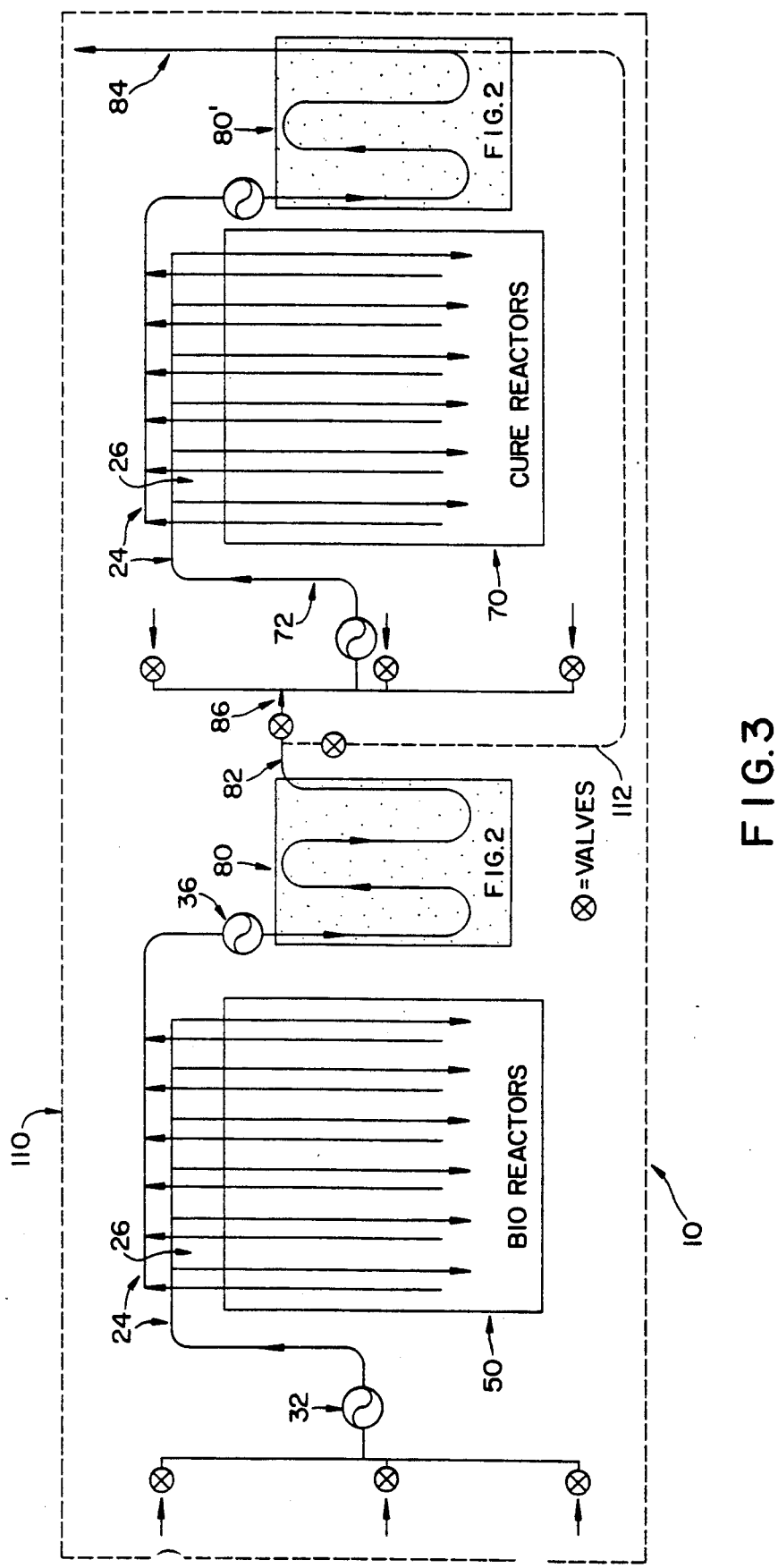
FIG. 3 is a schematic illustration of the fluid flow schematic for process, exhaust and odor control for a multiple train composting system.
Figure 4:
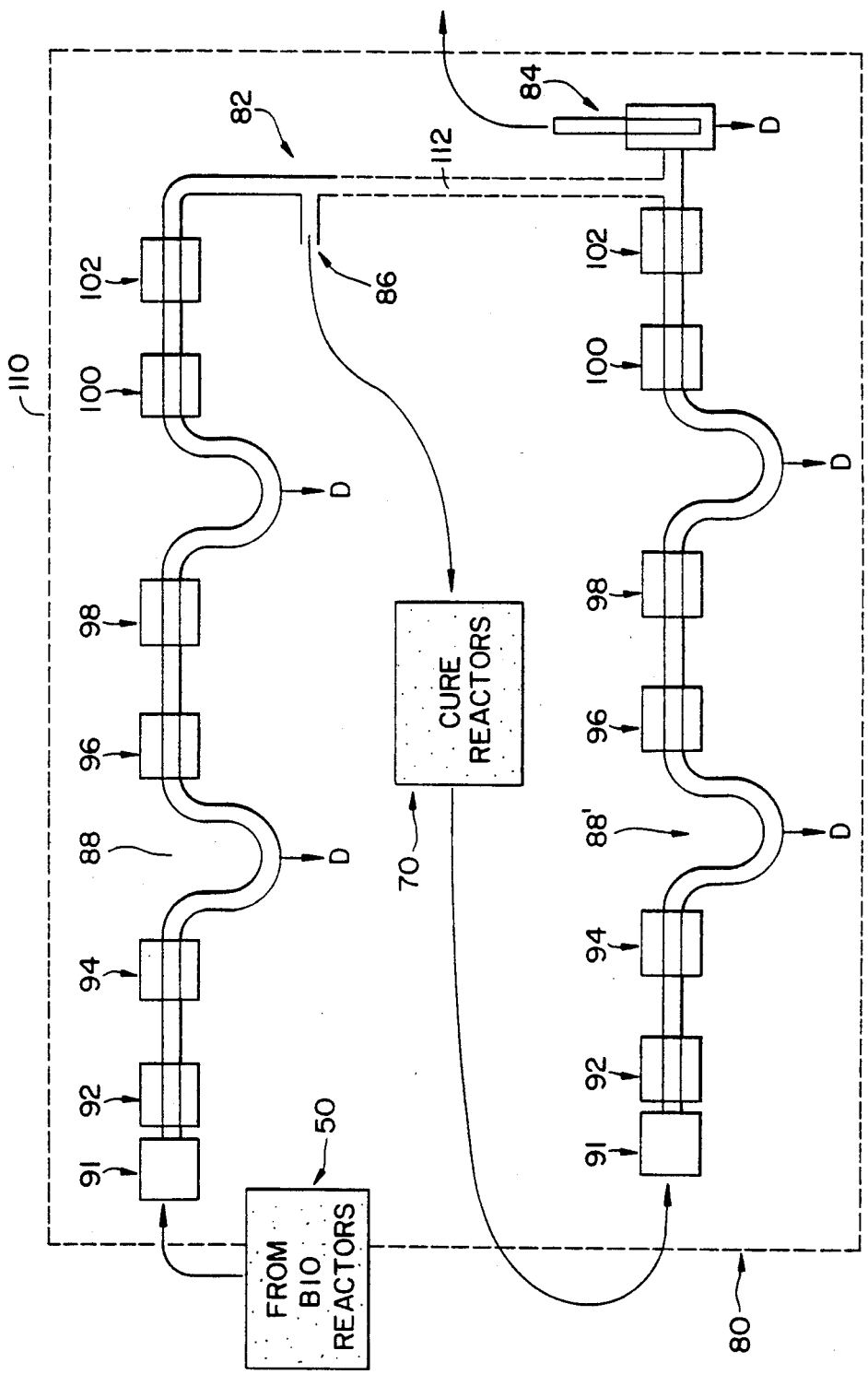
FIG. 4 is a schematic illustration of an embodiment of an odor control device for use in the in vessel composting system of FIG. 3.

Referring now to FIGS. 3 and 4, a multitrain system 110 is illustrated. The system 110 is very similar in operation to the system 10 and the same numerals are utilized for the same functions. The system 110 includes a second odor control device 80' and a second scrubbing train 88'. The system 110 also includes a bypass line 112 to exhaust excess air flow which is not needed by the cure reactor 70. This is determined by the temperature and drying requirements of the material in the reactor 70.

I claim as my invention:

1. A method for in-vessel composting of organic waste material comprising: providing an in-vessel system comprising a first compost reactor and a second compost reactor, said first compost reactor including a first organic waste containment vessel, and said first containment vessel having a first fluid injection and distribution means for injecting and evacuating process fluid in said first reactor, said first distribution means comprising a plurality of lance means for controlling flow of process fluid in the waste material, said second compost reactor including a second organic waste containment vessel, and said second containment vessel having a second fluid injection and distribution means for injecting and evacuating process fluid in said second reactor, said second distribution means comprising a plurality of said lance means, said lance means including a tubular outer porous wall and tubular inner fluid flow control insert concentrically positioned within said tubular inner flow control insert concentrically positioned within said tubular outer porous wall so as to define an annular space therebetween, at least one gasket sealingly engaged and adjustably mounted on said insert between said insert and said wall so as to divide said annular space into at least two variable zones, and said tubular insert also having a plurality of openings positioned along the length thereof so that each of said variable zones is in flow communication with at least one of said openings:
    introducing process fluid to said first reactor by injecting said process fluid through said first distribution means;
    exhausting at least partially spent process fluid from said first compost reactor by drawing it out of said first reactor through said first distribution means;
    passing at least a portion of said at least partially spent process fluid from said first reactor to said second reactor for use as process fluid for said second reactor.

2. A method for in-vessel composting of organic waste material comprising: providing an in-vessel system comprising a first compost reactor and a second compost reactor, said first compost reactor including a first organic waste containment vessel, and said first containment vessel having a first fluid injection and distribution means for injecting and evacuating process fluid in said first reactor, said first distribution means comprising a plurality of lance means for controlling flow of process fluid in the waste material, said second compost reactor including a second organic waste containment vessel, and said second containment vessel having a second fluid injection and distribution means for injecting and evacuating process fluid in said second reactor, said second distribution means comprising a plurality of said lance means, said lance means including a tubular outer porous wall and a tubular inner fluid flow control insert concentrically positioned within said tubular outer porous wall so as to define an annular space therebetween, at least one gasket sealingly engaged and adjustably mounted on said insert between said insert and said wall so as to divide said annular space into at least two variable zones, and said tubular insert also having a plurality of openings positioned along the length thereof so that each of said variable zones is in flow communication with at least one of said openings;
    (a) introducing process fluid to said first reactor by injecting said process fluid through said first distribution means;
    (b) exhausting at least partially spent process fluid from said first compost reactor by drawing it out of said first reactor through said first distribution means;
    (c) passing said at least partially spent process fluid from said first reactor through an odor control means for the removal of pollutants;
    (d) passing at least a portion of process fluid exhausted from the odor control means to the second reactor for use as process fluid for the second reactor.

3. The method of claim 2 wherein at least partially spent process fluid from the second compost reactor is recycled to the odor control means for treatment to remove pollutants.

4. The method of claim 2 wherein a portion of the process fluid exhausted from the odor control means is exhausted out of the system.

5. The method of claim 3 wherein a portion of the process fluid exhausted from the odor control means is exhausted out of the system.

6. The method of claim 2 wherein said odor control means is a plug flow design.

7. The method of claim 6 wherein said odor control means includes a fluid treatment train.

8. The method of claim 2 wherein said odor control means comprises at least one pollutant treatment zone capable of removing pollutants from said fluid.

9. The method of claim 8 wherein said odor control means comprises a plurality of pollutant treatment zones capable of removing pollutants.

10. The method of claim 9 wherein process fluid which is passed to said odor control means is first passed through a heat exchanger to lower the temperature of said fluid before it is passed to said odor control means.

11. The method of claim 9 wherein removal of pollutants form process fluid which passes through said odor control means comprises:
    passing process fluid exhausted from at least one of said first reactor or said second reactor to a first washing zone;
    passing the exhausted process fluid from said first washing zone to a second washing zone;
    passing the exhausted process fluid from said second washing zone to a first scrubbing zone;
    passing the exhausted process fluid from said first scrubbing zone to a third washing zone;
    passing the exhausted process fluid from said third washing zone to a second scrubbing zone;
    passing the exhausted process fluid from said second scrubbing zone to a fourth washing zone; and
    removing mist from the exhausted process fluid after passing through said fourth washing zone.

12. The method claim 11 wherein at least a portion of the exhausted process fluid is recycled to said second reactor for use as process fluid after passing through said fourth washing zone.

13. The method of claim 12 wherein at least a portion of the exhausted process fluid is emitted to the atmosphere after passing through said fourth washing zone.

14. The method of claim 7 wherein process fluid which is passed to said odor control means is first passed through a heat exchanger to lower the temperature of said fluid before it is passed to said odor control means.

15. The method of claim 14 wherein process fluid which is passed to said odor control means is first passed through a heat exchanger to lower the temperature of said fluid before it is passed to said odor control means.

16. An in-vessel system for composting organic waste material comprising: a first compost reactor and a second compost reactor, said first compost reactor inducing a first organic waste containment vessel, and said first containment vessel having a first fluid injection and distribution means for injecting and evacuating process fluid in said first reactor, said first distribution means comprising a plurality of lance means for controlling flow of process fluid in the waste material, said second compost reactor including a second organic waste containment vessel, and said second containment vessel having a second fluid injection and distribution means for injecting and evacuating process fluid in said second reactor, said second distribution means comprising a plurality of said lance means, said lance means including a tubular outer porous wall and a tubular inner fluid flow control insert concentrically positioned within said tubular outer porous wall so as to define an annular space therebetween, at least one gasket sealingly engaged and adjustably mounted on said insert between said insert and said wall so as to divide said annular space into at least two variable zones, and said tubular insert also having a plurality of openings positioned along the length thereof so that each of said variable zones is in flow communication with at least one of said openings, and odor control means for the removal of pollutants, said system further comprising;
    means for passing process fluid which is exhausted from said first reactor through said odor control means, and
    means for passing at least a portion of process fluid exhausted from said odor control means to said second reactor for use as process fluid in said second reactor.

17. The system of claim 16 further including means for recycling a portion of at least partially spent process fluid exhausted from said second reactor to said odor control means.

18. The system of claim 16 wherein said odor control means include a plug flow design.

19. The system of claim 16 wherein said odor control means include a fluid treatment train.

* * * * *